(12) United States Patent
Dieterle et al.

(10) Patent No.: US 7,022,877 B2
(45) Date of Patent: Apr. 4, 2006

(54) LONG-TERM OPERATION OF A HETEROGENEOUSLY CATALYZED GAS PHASE PARTIAL OXIDATION OF ACROLEIN TO ACRYLIC ACID

(75) Inventors: Martin Dieterle, Mannheim (DE); Jochen Petzoldt, Weisenheim am Berg (DE); Klaus Joachim Müller-Engel, Stutensee (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/962,570

(22) Filed: Oct. 13, 2004

(65) Prior Publication Data

US 2005/0096483 A1 May 5, 2005

Related U.S. Application Data

(60) Provisional application No. 60/514,918, filed on Oct. 29, 2003.

(30) Foreign Application Priority Data

Oct. 29, 2003 (DE) ................ 103 50 822

(51) Int. Cl.
*C07C 51/235* (2006.01)

(52) U.S. Cl. ...................... 562/532; 562/535

(58) Field of Classification Search .................. None
See application file for complete search history.

(56) References Cited

U.S. PATENT DOCUMENTS

| | | | |
|---|---|---|---|
| 5,442,108 A * | 8/1995 | Kawajiri et al. | ............ 562/532 |
| 5,739,391 A | 4/1998 | Ruppel et al. | |
| 6,403,829 B1 | 6/2002 | Unverricht et al. | |
| 2004/0150013 A1 | 8/2004 | Ipposhi | |

FOREIGN PATENT DOCUMENTS

| | | |
|---|---|---|
| DE | 44 31 949 A1 | 3/1995 |
| DE | 102 32 748 | 7/2002 |
| EP | 0 614 872 A1 | 9/1994 |
| EP | 0 990 636 A1 | 4/2000 |
| EP | 1 106 598 A2 | 6/2001 |
| WO | WO 00/53559 | 9/2000 |

* cited by examiner

*Primary Examiner*—Paul A. Zucker
(74) *Attorney, Agent, or Firm*—Oblon, Spivak, McClelland, Maier & Neustadt (57) ABSTRACT

A process for the long-term operation of a heterogeneously catalyzed gas phase partial oxidation of acrolein to acrylic acid, in which the temperature of the fixed catalyst bed is increased over time and partial oxidation is interrupted and an oxygen-containing gas is conducted through the fixed catalyst bed before the temperature increase is 8° C.

18 Claims, 3 Drawing Sheets

LONG-TERM OPERATION OF A HETEROGENEOUSLY CATALYZED GAS PHASE PARTIAL OXIDATION OF ACROLEIN TO ACRYLIC ACID

BACKGROUND OF THE INVENTION

1. Field of the Invention

The present invention relates to a process for the long-term operation of a heterogeneously catalyzed gas phase partial oxidation of acrolein to acrylic acid, by conducting a starting reaction gas mixture which comprises acrolein, molecular oxygen and at least one inert diluent gas through a fixed catalyst bed at elevated temperature whose catalysts are such that their active composition is at least one multimetal oxide which contains the elements Mo and V, and by, in order to counteract the deactivation of the fixed catalyst bed, increasing the temperature of the fixed catalyst bed over time.

2. Discussion of the Background

Acrylic acid is a reactive monomer which is suitable as such or in the form of its alkyl esters, for example, for preparing polymers which may find use as adhesives or water-absorbent materials, among other uses.

It is known that acrylic acid can be prepared on the industrial scale by a process for heterogeneously catalyzed gas phase partial oxidation of acrolein to acrylic acid, by conducting a starting reaction gas mixture comprising acrolein, molecular oxygen and at least one inert diluent gas through a fixed catalyst bed at elevated temperature whose catalysts are such that their active composition is at least one multimetal oxide which contains the elements Mo and V (cf., for example, DE-A 4431949, WO 0053559).

It is also known that such a process for heterogeneously catalyzed gas phase partial oxidation of acrolein to acrylic acid may be operated substantially continuously over prolonged periods over one and the same fixed catalyst bed. However, the fixed catalyst bed loses quality in the course of the operating time. In general, both its activity and the selectivity of target product formation deteriorate.

In order, despite this, to be able to operate the fixed catalyst beds, whose manufacturing and exchange is comparatively inconvenient and costly, for as long as possible in a reactor system charged with them, the prior art attempts in highly differing ways to counteract their aging process.

EP-A 990 636 (for example page 8, lines 13 to 15) and EP-A 1 106 598 (for example page 13, lines 43 to 45) propose the substantial compensation of the reduction in the quality of the particular fixed catalyst bed by gradually increasing the temperature of the particular fixed catalyst bed in the course of the operating time under otherwise substantially constant operating conditions, in order to substantially retain the acrolein conversion in single pass of the reaction gas mixture through the fixed catalyst bed.

In this context, the temperature of the fixed catalyst bed refers to the temperature of the fixed catalyst bed when the partial oxidation process is performed, except in the theoretical absence of a chemical reaction (i.e. without the influence of the heat of reaction). This also applies in this document. In contrast, effective temperature of the particular fixed catalyst bed refers in this document to the actual temperature of the fixed catalyst bed taking into account the heat of reaction of the partial oxidation. When the temperature of the fixed catalyst bed is not constant along the fixed catalyst bed (for example, in the case of a plurality of temperature zones), the term temperature of the fixed catalyst bed in this document means the (numerical) average of the temperature along the fixed catalyst bed.

It is significant in the aforementioned context that the temperature of the reaction gas mixture (and thus also the effective temperature of the fixed catalyst bed) passes through a maximum value (known as the hotspot value) when it passes through the fixed catalyst bed. The difference between hotspot value and the temperature of the fixed catalyst bed at the location of the hotspot value is referred to as the hotspot expansion.

A disadvantage of the procedure recommended in EP-A 990 636 and in EP-A 1 106 598 is that, with increasing increase in the temperature of the fixed catalyst bed, its aging process is accelerated (for example certain movement processes within the catalysts which contribute to aging proceed more rapidly). In general, this is in particular because hotspot expansion usually rises more steeply than the temperature of the fixed catalyst bed itself with an increase in the temperature of the fixed catalyst bed (cf., for example, page 12, lines 45 to 48 of EP-A 1 106 598 and page 8, lines 11 to 15 of EP-A 990 636). The effective temperature of the fixed catalyst bed therefore usually increases disproportionately in the hotspot region, which additionally promotes the aging of the fixed catalyst bed.

When a maximum value of the temperature of the fixed catalyst bed is attained, the fixed catalyst bed is therefore customarily fully exchanged.

However, a disadvantage of such a complete exchange is that it is comparatively costly and inconvenient. The process for preparing acrylic acid has to be interrupted for a prolonged time and the costs of catalyst preparation are likewise considerable.

Operating modes are therefore desired for processes for a heterogeneously catalyzed gas phase partial oxidation of acrolein to acrylic acid which are helpful in as far as possible prolonging the on-stream time of the fixed catalyst bed in the reactor system.

In this regard, DE-A 10 232 748 recommends, instead of fully exchanging the fixed catalyst bed, only replacing a portion thereof with a fresh catalyst charge.

A disadvantage of this proposal is that even a partial change of the fixed catalyst bed is accompanied by a significant cost and inconvenience.

EP-A 614 872 recommends extending the on-stream time of the fixed catalyst bed by, after operating the fixed catalyst bed for several years, which is accompanied by increases in the temperature thereof of from 15° C. to 30° C. and more, interrupting the process for partial oxidation, and, at fixed catalyst bed temperatures of from 260 to 450° C., conducting a gas mixture composed of oxygen, steam and inert gas through it, and subsequently continuing the partial oxidation.

In this context, inert gases in a gas mixture which is conducted through the fixed catalyst bed under certain conditions refers in this document to those gases of which at least 95 mol %, preferably at least 98 mol %, most preferably at least 99 mol % or 99.5 mol %, remains unchanged when they are conducted through the fixed catalyst bed. Regarding the gas mixture G to be used in accordance with the invention, steam and CO should not be included under the term inert gas.

However, a disadvantage of the procedure of EP-A 614 872 is that, up to the point at which the partial oxidation is interrupted, the aging of the fixed catalyst bed continues and is promoted unhindered.

SUMMARY OF THE INVENtION

It is an object of the present invention to provide a process for long-term operation of a heterogeneously catalyzed gas phase partial oxidation of acrolein to acrylic acid, in which the catalyst aging is counteracted in a way by which the intensity of the hotspot expansion over time is lower than in the prior art processes.

We have found that this object is achieved by a process for the long-term operation of a heterogeneously catalyzed gas phase partial oxidation of acrolein to acrylic acid, by conducting a starting reaction gas mixture which comprises acrolein, molecular oxygen and at least one inert diluent gas through a fixed catalyst bed at elevated temperature whose catalysts are such that their active composition is at least one multimetal oxide which contains the elements Mo and V, and by, in order to counteract the deactivation of the fixed catalyst bed, increasing the temperature of the fixed catalyst bed over time, which comprises interrupting the gas phase partial oxidation at least once before the temperature increase of the fixed catalyst bed is permanently $\geq 10°$ C., or $\geq 8°$ C., and, at a temperature of the fixed catalyst bed of from 200 to 450° C. (preferably from 250 to 400° C., often from 300 to 400° C, or from 250 to 350° C., or from 250 to 300° C.), conducting an acrolein-free, oxidizing gas mixture G comprising molecular oxygen, inert gas and optionally steam and also optionally CO through the fixed catalyst bed (the gas mixture G preferably consists substantially only, or only, of the aforementioned constituents).

DETAILED DESCRIPTION OF PREFERRED EMBODIMENTS

In this document, an oxidizing gas mixture G refers to a gas mixture G which, when the process according to the invention is employed, on entry into the fixed catalyst bed, does not reduce (but rather generally oxidizes) the oxidation states of the metals present in the multimetal oxide active composition.

In general, a gas mixture G therefore features a molar content of molecular oxygen on entry of the gas mixture G into the fixed catalyst bed which is larger than (preferably at least twice as large as) the sum of its molar content of CO and its molar contents of constituents other than CO, inert gas, $O_2$ and $H_2O$.

It is surprising that, when the process according to the invention is employed, long-term operation of a heterogeneously catalyzed gas phase partial oxidation of acrolein to acrylic acid is possible, by which the intensity of the hotspot expansion over time is lower than in the prior art processes. In favorable cases, the intensity of the hotspot expansion over time even decreases. In addition, the selectivity of acrylic acid formation usually remains substantially constant over time.

According to the invention, the gas phase partial oxidation will preferably be interrupted at least once even before the temperature increase of the fixed catalyst bed is permanently $\geq 7°$ C., or $\geq 6°$ C., or $\geq 5°$ C., or $\geq 4°$ C., in order to conduct an acrolein-free, oxidizing gas mixture G comprising molecular oxygen, inert gas and optionally steam and also optionally CO through the fixed catalyst bed at a temperature of the fixed catalyst bed of from 200 to 450° C.

In the process according to the invention, the gas phase partial oxidation will more preferably be interrupted at least once even before the temperature increase of the fixed catalyst bed is permanently $\geq 3°$ C. or $\geq 2°$ C., in order to conduct an acrolein-free, oxidizing gas mixture G comprising molecular oxygen, inert gas and optionally steam and also optionally CO through the fixed catalyst bed at a temperature of the fixed catalyst bed of from 200 to 450° C.

However, the process according to the invention is also advantageous when, before the temperature increase of the fixed catalyst bed is permanently $\geq 1°$ C. or less, the gas phase partial oxidation is interrupted at least once and an acrolein-free, oxidizing gas mixture G comprising molecular oxygen, inert gas and optionally steam and also optionally CO is conducted through the fixed catalyst bed at a temperature of from 200 to 450° C. However, the temperature increase of the fixed catalyst bed will generally be permanently $\geq 0.1°$ C. or $\geq 0.2°$ C. before the gas phase partial oxidation is interrupted at least once in accordance with the invention.

The temperature of the fixed catalyst bed while the gas mixture G is conducted through in the course of the performance of the process according to the invention will preferably be kept at a value $T_G$ which corresponds substantially to that temperature $T_V$ of the fixed catalyst bed at which the partial oxidation was operated before it was interrupted in order to conduct the gas mixture G through the fixed catalyst bed in accordance with the invention.

In other words, advantageously in accordance with the invention, $T_G = T_V \pm 50°$ C., or $T_G = T_V \pm 20°$ C., and, very particularly advantageously, $T_G = T_V$. Normally, $T_V$ will be in the range from 200 to 400° C., frequently in the range from 220 to 350° C. The duration $t_G$ over which the gas mixture G is to be conducted through the fixed catalyst bed in the process according to the invention will generally be from 2 h or 6 h to 120 h, frequently from 12 h to 72 h and in many cases from 20 h to 40 h. However, it may also be 10 days and more. In general, a smaller oxygen content of the gas mixture G will result in a longer duration $t_G$. Increased oxygen contents in the gas mixture G are advantageous in accordance with the invention.

Appropriately, the duration $t_G$ will at least be sufficiently long that the oxygen content of the gas mixture G when it enters and leaves the fixed catalyst bed will no longer differ.

Appropriately from an application point of view, the gas mixture G (all contents of the gas mixture G specified in this document relate, unless stated otherwise, to the entry of the gas mixture G into the fixed catalyst bed) in the process according to the invention will contain at least 1 or 2% by volume, preferably at least 3% by volume and more preferably at least 4% by volume, of oxygen. However the oxygen content of the gas mixture G will generally be $\leq 21\%$ by volume. In other words, a possible gas mixture G is air. Another possible gas mixture G is lean air. This is air depleted of oxygen. Advantageous in accordance with the invention is lean air which consists of from 3 to 10% by volume, preferably from 4 to 6% by volume, of oxygen, and a remainder of molecular nitrogen. It is frequently advantageous when the gas mixture G comprises not only molecular oxygen and inert gas, but also additionally steam. Appropriately from an application point of view, the gas mixture G contains at least 0.1% by volume, frequently at least 0.5% by volume, often at least 1% by volume, of steam. Normally, the steam content of the gas mixture G is ≦75% by volume. The inert gas content of the gas mixture G is generally ≦95% by volume, usually ≦90% by volume. Gas mixtures G which are suitable in accordance with the invention may thus consist, for example, of from 3 to 20% by volume of molecular oxygen, from 1 to 75% by volume of steam and a remainder of inert gas. Preferred inert gases are $N_2$ and $CO_2$. Useful gas mixtures G for the process according to the invention are in particular all of those recommended in EP-A 614 872. All regeneration conditions recommended in EP-A 614 872 may likewise be employed for the process according to the invention.

The CO content of a gas mixture G to be used in accordance with the invention will generally not exceed 5% by volume. Frequently, the CO content will be at values of ≦3% by volume, or ≦2% by volume, or ≦1% by volume, or be quite insignificant.

It has been found to be advantageous when the CO content C in the process according to the invention that the gas mixture G has on its entry into the fixed catalyst bed falls within the duration $t_G$ from a nonzero starting value A at the time $t_G=0$.

According to the invention, the CO content C preferably falls within the duration $t_G$ from its starting value A to a value E which is less than 50%, preferably less than 25%, more preferably less than 10% or less than 5%, of the starting value A. Very particularly preferably, the CO content C falls to a value of E=0.

The $CO_2$ content of the gas mixture G may also vary within the duration $t_G$ in a corresponding manner.

Conversely, it is advantageous for the process according to the invention when the oxygen content of the gas mixture G is raised within the duration $t_G$ starting from a lower value to a higher value.

Typically, it has been found to be advantageous to begin with an oxygen content of the gas mixture G of from about 1 to 3% by volume and to raise it within the duration $t_G$ to a value of up to 10% by volume, preferably up to 6% by volume. In contrast, a falling steam content of the gas mixture G duration the period $t_G$ is frequently selected. Starting values are in many cases up to 10% by volume, while the final value is frequently ≦3% by volume.

Gas mixtures G which are appropriate in accordance with the invention are therefore gas mixtures G* which contain:
from 1 to 8 (preferably from 3 to 6)% by volume of oxygen,
from 0 to 3% by volume of CO,
from 0 to 5% by volume of $CO_2$,
from 0 to 25% by volume of $H_2O$ and
at least 55% by volume of $N_2$ (G preferably consists of these constituents, in which case nitrogen then forms the remaining amount up to 100% by volume).

The $H_2O$, and also the CO and the $CO_2$ content of the gas mixture G* preferably decrease within $t_G$ as described, while the $O_2$ content increases as described. It has been found to be particularly advantageous when the gas mixture G on entry into the fixed catalyst bed has from >0 to ≦20 ppm by weight, frequently ≦15 or ≦10 or ≦5 or ≦1 ppm by weight, of gaseous Mo-containing compounds, for example molybdenum oxide hydrate. This content may be attained, for example, by passing a steam-containing gas mixture G at elevated temperature (e.g. 250–500° C.), before the inventive use, through a molybdenum oxide-containing bed.

The amount of the gas mixture G conducted through the fixed catalyst bed in the process according to the invention may be from 5 or 100 to 5000 l (STP)/l·h, preferably from 20 or 200 to 2000 l (STP)/l·h (the reference basis is the volume of the overall fixed catalyst bed, i.e. including any sections used which consist exclusively of inert material).

In general, the gas mixture G will be conducted through the fixed catalyst bed in the process according to the invention at a temperature of the fixed catalyst bed of from 200 to 450° C. in a frequency F of at least once per calendar year, preferably of at least once per three-quarter calendar year or per half calendar year, more preferably at least once per calendar quarter and more preferably of at least once per calendar month. Otherwise, the process for heterogeneously catalyzed gas phase partial oxidation of acrolein to acrylic acid will be carried out substantially continuously.

In other words, the gas mixture G will be conducted through the fixed catalyst bed in the process according to the invention at a temperature of the fixed catalyst bed of from 200 to 450° C. at least once within 7500 or 7000, or 6000, preferably at least once within 5500 or 5000 and most preferably at least once within 4000, or 3000 or 2000 or 1500, or 1000, or 500, operating hours of the partial oxidation. Carrying out the process according to the invention frequently has an advantageous effect.

Suitable active compositions for the catalysts of the fixed catalyst bed are, as is well known, multimetal oxides which comprise the elements Mo and V.

Multimetal oxide active compositions comprising Mo and V which are suitable in accordance with the invention may be taken, for example, from U.S. Pat. No. 3,775,474, U.S. Pat. No. 3,954,855, U.S. Pat. No. 3,893,951, and U.S. Pat. No. 4,339,355, or EP-A 614872 or EP-A 1041062, or WO 03/055835, or WO 03/057653.

Especially suitable are also the multimetal oxide active compositions of DE-A 10 325 487 and also of DE-A 10 325 488.

Also particularly suitable as active compositions for fixed bed catalysts suitable for the process according to the invention are the multimetal oxide compositions of EP-A 427 508, DE-A 2 909 671, DE-C 31 51 805, DE-B 2 626 887, DE-A 43 02 991, EP-A 700 893, EP-A 714 700 and DE-A 19 73 6105. Particular preference is given in this context to the exemplary embodiments of EP-A 714 700 and of DE-A 19 73 6105.

A multitude of these multimetal oxide active compositions suitable for said fixed bed catalysts can be encompassed by the general formula I $$Mo_{12}V_aX^1_bX^2_cX^3_dX^4_eX^5_fX^6_gO_n \qquad (I)$$

in which the variables are defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in I other than oxygen.

Preferred embodiments among the active multimetal oxides I are those which are encompassed by the following definitions of the variables of the general formula I:

$X^1$=W, Nb and/or Cr,
$X^2$=Cu, Ni, Co and/or Fe,
$X^3$=Sb,
$X^4$=Na and/or K,
$X^5$=Ca, Sr and/or Ba,
$X^5$=Si, Al and/or Ti,
a=from 1.5 to 5,
b=from 0.5 to 2,
c=from 0.5 to 3,
d=from 0 to 2,
e=from 0 to 0.2,
f=from 0 to 1 and
n=a number which is determined by the valency and frequency of the elements in I other than oxygen.

However, multimetal oxides I which are very particularly preferred according to the invention are those of the general formula II (II)

where
$Y^1$=W and/or Nb,
$Y^2$=Cu and/or Ni,
$Y^5$=Ca and/or Sr,
$Y^6$=Si and/or Al,
a'=from 2 to 4,
b'=from 1 to 1.5,
c'=from 1 to 3,
f'=from 0 to 0.5
g'=from 0 to 8 and
n'=a number which is determined by the valency and frequency of the elements in II other than oxygen.

The multimetal oxide active compositions (I) which are suitable according to the invention are obtainable in a manner known per se, for example disclosed in DE-A 4335973 or in EP-A 714700. However, the multimetal oxide active compositions of DE-A 10 261 186 are also especially suitable.

In principle, suitable multimetal oxide active compositions for fixed bed catalysts to be used for the process according to the invention, in particular those of the general formula I, can be prepared in a simple manner by obtaining a very intimate, preferably finely divided dry mixture having a composition corresponding to their stoichiometry from suitable sources of their elemental constituents and calcining it at temperatures of from 350 to 600° C. The calcination may be carried out either under inert gas or under an oxidative atmosphere, for example air (mixture of inert gas and oxygen), and also under a reducing atmosphere (for example mixtures of inert gas and reducing gases such as $H_2$, $NH_3$, CO, methane and/or acrolein or the reducing gases mentioned themselves). The calcination time can be from a few minutes to a few hours and typically decreases with temperature. Useful sources for the elemental constituents of the multimetal oxide active compositions I include those compounds which are already oxides and/or those compounds which can be converted to oxides by heating, at least in the presence of oxygen.

The starting compounds for preparing multimetal oxide compositions I can be intimately mixed in dry or in wet form. When they are mixed in dry form, the starting compounds are advantageously used as finely divided powder and subjected to calcining after mixing and optional compaction. However, preference is given to intimate mixing in wet form.

This is typically done by mixing the starting compounds in the form of an aqueous solution and/or suspension. Particularly intimate dry mixtures are obtained in the mixing process described when the starting materials are exclusively sources of the elemental constituents in dissolved form. The solvent used is preferably water. Subsequently, the aqueous composition obtained is dried, and the drying process is preferably effected by spray-drying the aqueous mixture at exit temperatures of from 100 to 150° C.

The suitable multimetal oxide active compositions for fixed bed catalysts to be used for the process according to the invention, in particular those of the general formula 1, may be used for the process according to the invention either in powder form or shaped to certain catalyst geometries, and the shaping may be effected before or after the final calcination. For example, unsupported catalysts can be prepared from the powder form of the active composition or its uncalcined precursor composition by compacting to the desired catalyst geometry (for example by tableting or extruding), optionally with the addition of assistants, for example graphite or stearic acid as lubricants and/or shaping assistants and reinforcing agents such as microfibers of glass, asbestos, silicon carbide or potassium titanate. Examples of suitable unsupported catalyst geometries are solid cylinders or hollow cylinders having an external diameter and a length of from 2 to 10 mm. In the case of the hollow cylinder, a wall thickness of from 1 to 3 mm is advantageous. It will be appreciated that the unsupported catalyst may also have spherical geometry and the spherical diameter may be from 2 to 10 mm.

It will be appreciated that the pulverulent active composition or its pulverulent precursor composition which is yet to be calcined can also be shaped by applying to preshaped inert catalyst supports. The coating of the support bodies to prepare the coated catalysts is generally performed in a suitable rotatable vessel, as disclosed, for example, by DE-A 2909671, EP-A 293859 or from EP-A 714700.

To coat the support bodies, the powder composition to be applied is appropriately moistened and is dried again after application, for example by means of hot air. The coating thickness of the powder composition applied to the support body is advantageously selected within the range from 10 to 1000 μm, preferably within the range from 50 to 500 μm and more preferably in the range from 150 to 250 μm.

Useful support materials are customary porous or nonporous aluminum oxides, silicon dioxide, thorium dioxide, zirconium dioxide, silicon carbide or silicates such as magnesium silicate or aluminum silicate. The support bodies may have a regular or irregular shape, although preference is given to regularly shaped support bodies having distinct surface roughness, for example spheres or hollow cylinders. It is suitable to use substantially nonporous, surface-roughened, spherical supports made of steatite whose diameter is from 1 to 8 mm, preferably from 4 to 5 mm. However, suitable support bodies also include cylinders whose length is from 2 to 10 mm and whose external diameter is from 4 to 10 mm. In the case of rings which are suitable according to the invention as support bodies, the wall thickness is also typically from 1 to 4 mm.

Annular support bodies to be used with preference in accordance with the invention have a length of from 3 to 6 mm, an external diameter of from 4 to 8 mm and a wall thickness of from 1 to 2 mm. Suitable support bodies according to the invention are also in particular rings of geometry 7 mm×3 mm×4 mm (external diameter x length x internal diameter). It will be appreciated that the fineness of the catalytically active oxide compositions to be applied to the surface of the support body is adapted to the desired coating thickness (cf. EP-A 714 700).

Advantageous multimetal oxide active compositions to be used for fixed bed catalysts which are suitable for the process according to the invention are also compositions of the general formula III $$[D]_p[E]_q \qquad (III)$$

in which the variables are defined as follows:
$D=Mo_{12}V_{a''}Z^1_{b''}Z^2_{c''}Z^3_{d''}Z^4_{e''}Z^5_{f''}Z^{6''}O_{x'''}$,
$E=Z^7_{12}Cu_{h''}H_{i''}O_{y'''}$,
$Z^1$=W, Nb, Ta, Cr and/or Ce,
$Z^2$=Cu, Ni, Co, Fe, Mn and/or Zn,
$Z^3$=Sb and/or Bi,
$Z^4$=Li, Na, K, Rb, Cs and/or H,
$Z^5$=Mg, Ca, Sr and/or Ba,
$Z^6$=Si, Al, Ti and/or Zr,
$Z^7$=Mo, W, V, Nb and/or Ta,
a''=from 1 to 8,
b''=from 0.2 to 5,
c''=from 0 to 23,
d''=from 0 to 50,
e''=from 0 to 2,
f''=from 0 to 5,
g''=from 0 to 50,
h''=from 4 to 30,
i''=from 0 to 20 and
x'',y''=numbers which are determined by the valency and frequency of the elements other than oxygen in III and
p,q=numbers other than zero whose p/q ratio is from 160:1 to 1:1, and which are obtainable by separately performing a multimetal oxide composition E $$Z^7_{12}Cu_{h''}H_{i''}O_{y''} \qquad (E)$$

in finely divided form (starting composition 1) and subsequently incorporating the preformed solid starting composition 1 into an aqueous solution, an aqueous suspension or into a finely divided dry mixture of sources of the elements Mo, V, $Z^1$, $Z^2$, $Z^3$, $Z^4$, $Z^5$, $Z^6$ which comprises the abovementioned elements in the stoichiometry D $$Mo_{12}V_{a''}Z^1_{b''}Z^2_{c''}Z^3_{d''}Z^4_{e''}Z^5_{f''}Z^6_{g''} \qquad (D)$$

(starting composition 2) in the desired p:q ratio, drying the aqueous mixture which may result, and calcining the resulting dry precursor composition before or after drying at temperatures of from 250 to 600° C. to give the desired catalyst geometry.

Preference is given to those multimetal oxide active compositions III in which the preformed solid starting composition 1 is incorporated into an aqueous starting composition 2 at a temperature of <70° C. A detailed description of the preparation of multimetal oxide composition III catalysts is contained, for example, in EP-A 668104, DE-A 19736105, and DE-A 19528646.

With regard to the shaping, the statements made for the multimetal oxide active composition I catalysts apply to the multimetal oxide active composition III catalysts.

Advantageous multimetal oxide active compositions for the catalysts of the fixed bed catalyst of the process according to the invention are also multielement oxide active compositions of the general formula IV $$[A]_p[B]_q[C]_r \qquad (IV)$$

in which the variables are each defined as follows:
$A=Mo_{12}V_aX^1_bX^2_cX^3_dX^4_eX^5_fX^6_gO_x$,
$B=X^7_1Cu_hH_iO_y$,
$C=X^8_1Sb_jH_kO_z$,
$X^1$=W, Nb, Ta, Cr and/or Ce, preferably W, Nb and/or Cr,
$X^2$=Cu, Ni, Co, Fe, Mn and/or Zn, preferably Cu, Ni, Co and/or Fe,
$X^3$=Sb and/or Bi, preferably Sb,
$X^4$=Li, Na, K, Rb, Cs and/or H, preferably Na and/or K,
$X^5$=Mg, Ca, Sr and/or Ba, preferably Ca, Sr and/or Ba,
$X^6$=Si, Al, Ti and/or Zr, preferably Si, Al and/or Ti,
$X^7$=Mo, W, V, Nb and/or Ta, preferably Mo and/or W,
$X^8$=Cu, Ni, Zn, Co, Fe, Cd, Mn, Mg, Ca, Sr and/or Ba, preferably Cu and/or Zn, more preferably Cu,
a=from 1 to 8, preferably from 2 to 6,
b=from 0.2 to 5, preferably from 0.5 to 2.5
c=from 0 to 23, preferably from 0 to 4,
d=from 0 to 50, preferably from 0 to 3,
e=from 0 to 2, preferably from 0 to 0.3,
f=from 0 to 5, preferably from 0 to 2,
g=from 0 to 50, preferably from 0 to 20,
h=from 0.3 to 2.5, preferably from 0.5 to 2, more preferably from 0.75 to 1.5,
i=from 0 to 2, preferably from 0 to 1,
j=from 0.1 to 50, preferably from 0.2 to 20, more preferably from 0.2 to 5,
k=from 0 to 50, preferably from 0 to 20, more preferably from 0 to 12,
x,y,z=numbers which are determined by the valency and frequency of the elements in A, B, C other than oxygen,
p, q=positive numbers r=0 or a positive number, preferably a positive number, where the p/(q+r) ratio=from 20:1 to 1:20, preferably from 5:1 to 1:14 and more preferably from 2:1 to 1:8 and, in the case that r is a positive number, the q/r ratio=from 20:1 to 1:20, preferably from 4:1 to 1:4, more preferably from 2:1 to 1:2 and most preferably 1:1, which contain the fraction $[A]_p$ in the form of three-dimensional regions (phases) A of the chemical composition $A: Mo_{12}VaX^1_bX^2_cX^3_dX^4_eX^5_fX^6_gO_x$, the fraction $[B]_q$ in the form of three-dimensional regions (phases) B of the chemical composition $B: X^7_1CU_hH_iO_y$, and the fraction $[C]_r$ in the form of three-dimensional regions (phases) C of the chemical composition $C: X^8_1Sb_jH_kO_z$, where the regions A, B and, where present, C are distributed relative to each other as in a mixture of finely divided A, finely divided B and, where present, finely divided C, and where all variables are to be selected within the predefined ranges with the proviso that the molar fraction of the element Mo in the total amount of all elements in the multielement oxide active composition IV other than oxygen is from 20 mol % to 80 mol %, the molar ratio of Mo present in the catalytically active multielement oxide composition IV to V present in the catalytically active multielement oxide composition IV, Mo/V, is from 15:1 to 1:1, the corresponding molar Mo/Cu ratio is from 30:1 to 1:3 and the corresponding molar Mo/(total amount of W and Nb) ratio is from 80:1 to 1:4.

Preferred multielement oxide active compositions IV are those whose regions A have a composition within the following stoichiometric pattern of the general formula V:

$$Mo_{12}V_a X^1_b X^2_c X^5_f X^6_g O_x \qquad (V)$$

where
X$^1$=W and/or Nb,
X$^2$=Cu and/or Ni,
X$^5$=Ca and/or Sr,
X$^6$=Si and/or Al,
a=from 2 to 6,
b=from 1 to 2,
c=from 1 to 3,
f=from 0 to 0.75,
g=from 0 to 10, and
x=a number which is determined by the valency and frequency of the elements in (V) other than oxygen.

The term "phase" used in connection with the multielement oxide active compositions V means three-dimensional regions whose chemical composition is different from that of their environment. The phases are not necessarily x-ray-homogeneous. In general, phase A forms a continuous phase in which particles of phase B and, where present, C are dispersed.

The finely divided phases B and, where present, C advantageously consist of particles whose largest diameter, i.e. longest line passing through the center of the particles and connecting two points on the surface of the particles, is up to 300 μm, preferably from 0.1 to 200 μm, more preferably from 0.5 to 50 μm and most preferably from 1 to 30 μm. However, particles having a longest diameter of from 10 to 80 μm or from 75 to 125 μm are also suitable.

In principle, the phases A, B and, where present, C may be in amorphous and/or crystalline form in the multielement oxide active compositions IV.

The intimate dry mixtures on which the multielement oxide active compositions of the general formula IV are based and are subsequently to be treated thermally to convert them to active compositions may be obtained, for example, as described in the documents WO 02/24327, DE-A 4405514, DE-A 4440891, DE-A 19528646, DE-A 19740493, EP-A 756894, DE-A 19815280, DE-A 19815278, EP-A 774297, DE-A 19815281, EP-A 668104 and DE-A 19736105.

The basic principle of preparing intimate dry mixtures whose thermal treatment leads to multielement oxide active compositions of the general formula IV is to perform, in finely divided form, separately or combined together, at least one multielement oxide composition B (X$_1^7$CU$_h$H$_i$O$_y$) as the starting composition 1 and, where appropriate, one or more multielement oxide compositions C (X$_1^8$Sb$_j$H$_k$O$_z$) as the starting composition 2, and subsequently to intimately contact, in the desired ratio (corresponding to the general formula IV), the starting compositions 1 and, where appropriate, 2 with a mixture, which comprises sources of the elemental constituents of the multielement oxide composition A $$Mo_{12}V_a X_b^1 X_c^2 X_d^3 X_e^4 X_f^5 X_g^6 O_x \qquad (A)$$

in a composition corresponding to the stoichiometry A, and optionally to dry the resulting intimate mixture.

The intimate contacting of the constituents of the starting compositions 1 and, where appropriate, 2 with the mixture comprising the sources of the elemental constituents of the multimetal oxide composition A (starting composition 3) may be effected either in dry or in wet form. In the latter case, care has to be taken merely that the preformed phases (crystallites) B and, where appropriate, C do not go into solution. In an aqueous medium, the latter is usually ensured at pH values which do not deviate too far from 7 and at temperatures which are not excessively high. When the intimate contacting is effected in wet form, there is normally final drying to give the intimate dry mixture to be thermally treated in accordance with the invention (for example by spray-drying). In the case of dry mixing, such a dry mass is obtained automatically. It will be appreciated that the phases B and, where appropriate, C preformed in finely divided form may also be incorporated into a plastically reshapeable mixture which comprises the sources of the elemental constituents of the multimetal oxide composition A, as recommended by DE-A 10046928. The intimate contacting of the constituents of the starting compositions 1 and, where appropriate, 2 with the sources of the multielement oxide composition A (starting composition 3) may of course also be effected as described in DE-A 19815281.

The thermal treatment to obtain the active composition and the shaping may be effected as described for the multimetal oxide active compositions I to III.

Quite generally, multimetal oxide active composition I to IV catalysts may advantageously be prepared in accordance with the teaching of DE-A 10 325 487 or DE-A 10 325 488.

Appropriately from an application point of view, the process according to the invention for heterogeneously catalyzed gas phase partial oxidation of acrolein to acrylic acid will be carried out in a tube bundle reactor charged with the fixed bed catalysts, as described, for example, in EP-A 700 893 or DE-A 4 431 949 or WO 03/057653, or WO 03/055835, or WO 03/059857, or WO 03/076373.

In other words, in the simplest manner, the fixed catalyst bed to be used in the process according to the invention is disposed in the uniformly charged metal tubes of a tube bundle reactor and a heating medium (one-zone method), generally a salt melt, is conducted around the metal tubes. Salt melt (heating medium) and reaction gas mixture may be conducted in simple co- or countercurrent. However, the heating medium (the salt melt) may also be conducted around the tube bundle in a meandering manner viewed over the reactor, so that only viewed over the entire reactor does a co- or countercurrent to the flow direction of the reaction gas mixture exist. The volume flow rate of the heating medium (heat exchange medium) is typically such that the temperature rise (caused by the exothermicity of the reaction) of the heat exchange medium from the inlet point into the reactor to the outlet point from the reactor is from 0 to 10° C., frequently from 2 to 8° C., often from 3 to 6° C. The inlet temperature of the heat exchange medium into the tube bundle reactor (in this document, this corresponds to the temperature of the fixed catalyst bed) is generally from 220 to 350° C., frequently from 245 to 285° C. or from 245 to 265° C. Suitable heat exchange media are in particular fluid heating media. It is particularly appropriate to use melts of salt such as potassium nitrate, potassium nitrite, sodium nitrite and/or sodium nitrate, or of low-melting metals such as sodium, mercury and also alloys of different metals. Ionic liquids can also be used.

Appropriately, the reaction gas mixture is fed to the charge of fixed bed catalyst preheated to the desired reaction temperature.

Especially in the case of the desired high (e.g. ≧140 l (STP)/l·h, but generally ≦600 l (STP)/l·h) final hourly space velocities of acrolein on the fixed catalyst bed, the process according to the invention is appropriately carried out in a two-zone tube bundle reactor (however, it is likewise possible to carry it out in a one-zone tube bundle reactor). A preferred variant of a two-zone tube bundle reactor which can be used for this purpose in accordance with the invention is disclosed by DE-C 2830765. However, the two-zone tube bundle reactors disclosed in DE-C 2513405, U.S. Pat. No. 3,147,084, DE-A 2201528, EP-A 383224 and DE-A 2903582 are also suitable.

In other words, in a simple manner, the fixed catalyst bed to be used in accordance with the invention is disposed in the uniformly charged metal tubes of a tube bundle reactor and two substantially spatially separated heating media, generally salt melts, are conducted around the metal tubes. The tube section over which the particular salt bath extends represents a temperature or reaction zone.

For example, salt bath A preferably flows around that section of the tubes (the reaction zone A) in which the oxidative conversion of acrolein (in single pass) proceeds until a conversion value in the range from 55 to 85 mol % is achieved and a salt bath B preferably flows around the section of the tubes (reaction zone B) in which the subsequent oxidative conversion of acrolein (in single pass) proceeds until a conversion value of generally at least 90 mol % is achieved (if required, the reaction zones A, B may be followed by further reaction zones which are kept at individual temperatures).

Within the particular temperature zone, the salt bath may in principle be conducted as in the one-zone method. The inlet temperature of the salt bath B is normally from at least 5 to 10° C. above the temperature of the salt bath A. Otherwise, the inlet temperatures may be within the temperature range for the inlet temperature recommended for the one-zone method.

Otherwise, the two-zone high-load method may be carried out as described, for example, in DE-A 19948523, EP-A 1106598 or as described in DE-A 19948248.

Accordingly, the process according to the invention is suitable for acrolein hourly space velocities on the fixed catalyst bed of $\geq 70$ l (STP)/l·h, $\geq 90$ l (STP)/l·h, $\geq 110$ l (STP)/l·h, $\geq 130$ l (STP)/l·h, $\geq 180$ l (STP)/l·h, $\geq 240$ l (STP)/l·h, $\geq 300$ l (STP)/l·h, but normally $\geq 600$ l (STP)/l·h. Here (i.e. generally in the case of acrolein hourly space velocities in this document), in a departure from the norm in this document, the hourly space velocity is based on the volume of the fixed catalyst bed excluding any sections used which consist exclusively of inert material.

The inert gas to be used for the charge gas mixture may consist of, for example, $\geq 20\%$ by volume, or $\geq 30\%$ by volume, or $\geq 40\%$ by volume, or $\geq 50\%$ by volume, or $\geq 60\%$ by volume, or $\geq 70\%$ by volume, or $\geq 80\%$ by volume, or $\geq 90\%$ by volume, or $\geq 95\%$ by volume, of molecular nitrogen.

However, when the gas phase partial oxidation of acrolein is the second reaction stage of a two-stage gas phase partial oxidation of propene to acrylic acid, the inert diluent gas will frequently consist of from 5 to 25 or 20% by weight of $H_2O$ (is formed in the first reaction stage and optionally added) and of from 70 to 90% by volume of $N_2$.

However, at acrolein hourly space velocities on the fixed catalyst bed of above 250 l (STP)/l·h, the use of inert diluent gases such as propane, ethane, methane, butane, pentane, $CO_2$, CO, steam and/or noble gases is recommended for the process according to the invention. However, it will be appreciated that these gases may also be used even at relatively low acrolein hourly space velocities.

The working pressure in the inventive gas phase partial oxidation of acrolein may be either below atmospheric pressure (for example up to 0.5 bar) or above atmospheric pressure. Typically, the working pressure in the gas phase partial oxidation of acrolein will be at values of from 1 to 5 bar, frequently from 1 to 3 bar.

Normally, the reaction pressure in the inventive acrolein partial oxidation will not exceed 100 bar.

The molar $O_2$:acrolein ratio in the starting reaction gas mixture which is conducted through the fixed catalyst bed in the process according to the invention will normally be $\geq 1$. Typically, this ratio will be at values of $\leq 3$. According to the invention, the molar $O_2$:acrolein ratio in the aforementioned charge gas mixture will frequently be from 1 to 2 or from 1 to 1.5. In many cases, the process according to the invention will be performed at an acrolein:oxygen:steam:inert gas volume ratio (l (STP)) present in the starting reaction gas mixture of 1:(1 to 3):(0 to 20):(3 to 30), preferably of 1:(1 to 3):(0.5 to 10):(7 to 10).

The acrolein fraction in the starting reaction gas mixture may be, for example, at values of from 3 or 6 to 15% by volume, frequently from 4 or 6 to 10% by volume, or from 5 to 8% by volume (based in each case on the total volume). To prepare the fixed catalyst bed to be used in the process according to the invention only the appropriate shaped catalyst bodies having multimetal oxide active composition or else substantially homogeneous mixtures of shaped catalyst bodies having multimetal oxide active composition and shaped bodies having no multimetal oxide active composition which behave substantially inertly with respect to the heterogeneously catalyzed partial gas phase oxidation (and consist of inert material) (shaped diluent bodies). Useful materials for such inert shaped bodies are in principle all of those which are also suitable as support materials for coated catalysts which are suitable in accordance with the invention. Useful such materials are, for example, porous or nonporous aluminum oxides, silicon dioxide, thorium dioxide, zirconium dioxide, silicon carbide, silicates such as magnesium or aluminum silicate or the steatite already mentioned (for example Steatite C-220 from CeramTec).

The geometry of such inert shaped diluent bodies may in principle be as desired. In other words, they may be, for example, spheres, polygons, solid cylinders or else rings. According to the invention, the inert shaped diluent bodies selected will preferably be those whose geometry corresponds to that of the shaped catalyst bodies to be diluted by them.

In general, it is favorable when the chemical composition of the active composition used does not change over the fixed catalyst bed. In other words, although the active composition used for an individual shaped catalyst body may be a mixture of different multimetal oxides comprising the elements Mo and V, the same mixture then advantageously has to be used for all shaped catalyst bodies of the fixed catalyst bed.

The volume-specific (i.e. normalized to the unit of volume) activity preferably normally increases continuously, abruptly or stepwise within the fixed catalyst bed in the flow direction of the starting reaction gas mixture.

The volume-specific activity may, for example, be reduced in a simple manner by homogeneously diluting a basic amount of shaped catalyst bodies prepared in a uniform manner with shaped diluent bodies. The higher the fraction of the shaped diluent bodies selected, the lower the amount of active composition, i.e. catalyst activity, in a certain volume of the fixed bed.

A volume-specific activity increasing at least once in the flow direction of the reaction gas mixture over the fixed catalyst bed can thus be attained in a simple manner for the process according to the invention, for example, by beginning the bed with a high fraction of inert shaped diluent bodies based on one type of shaped catalyst bodies, and then reducing this fraction of shaped diluent bodies in the flow direction either continuously or, at least once or more than once, abruptly (for example in stages). However, an increase in the volume-specific activity is also possible, for example, by, at constant geometry and active composition type of a shaped coated catalyst body, increasing the thickness of the active composition layer applied to the support, or, in a mixture of coated catalysts having the same geometry but having different proportions by weight of the active composition, increasing the fraction of shaped catalyst bodies having a higher proportion by weight of active composition. Alternatively, the active compositions themselves may also be diluted by, in the course of active composition preparation, for example, incorporating inert diluting materials such as hard-fired silicon dioxide into the dry mixture of starting compounds to be calcined. Different addition amounts of diluting material automatically lead to different activities. The more diluting material is added, the lower the resulting activity will be. A similar effect can also be achieved, for example, by appropriately varying the mixing ratio in mixtures of unsupported catalysts and of coated catalysts (with identical active composition). It will be appreciated that the variants described may also be employed in combination.

Of course, mixtures of catalysts having chemically different active compositions and, as a consequence of this different composition, different activities may also be used for the fixed catalyst bed. These mixtures may in turn be diluted with inert diluent bodies.

Upstream and/or downstream of the sections of the fixed catalyst bed having active composition may be disposed beds consisting exclusively of inert material (for example only shaped diluent bodies) (in this document, they are included for terminology purposes in the fixed catalyst bed, unless stated otherwise). These may likewise be brought to the temperature of the fixed catalyst bed. The shaped diluent bodies used for the inert bed may have the same geometry as the shaped catalyst bodies used for the sections of the fixed catalyst bed having active composition. However, the geometry of the shaped diluent bodies used for the inert bed may also be different to the aforementioned geometry of the shaped catalyst bodies (for example, spherical instead of annular).

Frequently, the shaped bodies used for such inert beds have the annular geometry 7 mm×7 mm×4 mm (external diameter×length×internal diameter) or the spherical geometry having the diameter d=4–5 mm.

In many cases, the section of the fixed catalyst bed having active composition is structured as follows in the flow direction of the reaction gas mixture in the process according to the invention.

First, to a length of from 10 to 60%, preferably from 10 to 50%, more preferably from 20 to 40% and most preferably from 25 to 35% (i.e. for example, to a length of from 0.70 to 1.50 m, preferably from 0.90 to 1.20 m), each of the total length of the section of the fixed catalyst bed having active composition, one homogeneous mixture or two successive homogeneous mixtures (having decreasing dilution) of shaped catalyst bodies and shaped diluent bodies (both preferably having substantially the same geometry), in which the proportion by weight of shaped diluent bodies (the mass densities of shaped catalyst bodies and of shaped diluent bodies generally differ only slightly) is normally from 10 to 50% by weight, preferably from 20 to 45% by weight and more preferably from 25 to 35% by weight. Downstream of this first zone is then frequently advantageously disposed, up to the end of the length of the section of the fixed catalyst bed having active composition (i.e., for example, to a length of from 2.00 to 3.00 m, preferably from 2.50 to 3.00 m), either a bed of shaped catalyst bodies diluted only to a lesser extent (than in the first zone), or, most preferably, a sole bed of the same shaped catalyst bodies which have also been used in the first zone.

The aforementioned is especially true when the shaped catalyst bodies used in the fixed catalyst bed are coated catalyst rings or coated catalyst spheres (especially those which are listed in this document as preferred). For the purposes of the aforementioned structuring, both the shaped catalyst bodies or their support rings and the shaped diluent bodies in the process according to the invention advantageously have substantially the ring geometry 7 mm×3 mm×4 mm (external diameter×length×internal diameter).

The aforementioned is also true when, instead of inert shaped diluent bodies, shaped coated catalyst bodies are used whose active composition content is from 2 to 15% by weight lower than the active composition content of the shaped coated catalyst bodies at the end of the fixed catalyst bed.

A pure inert material bed whose length, based on the total length of the fixed catalyst bed, is appropriately from 5 to 20% generally begins the fixed catalyst bed in the flow direction of the reaction gas mixture. It is normally used as a heating zone for the reaction gas mixture.

Typically, the catalyst tubes in the tube bundle reactors are manufactured from ferritic steel and typically have a wall thickness of from 1 to 3 mm. Their internal diameter is generally (uniformly) from 20 to 30 mm, frequently from 21 to 26 mm. Appropriately from an application point of view, the number of catalyst tubes accommodated in the tube bundle vessel is at least 5000, preferably at least 10 000. Frequently, the number of catalyst tubes accommodated in the reaction vessel is from 15 000 to 30 000. Tube bundle reactors having a number of catalyst tubes above 40 000 are usually exceptional. Within the vessel, the catalyst tubes are normally arranged in homogeneous distribution, and the distribution is appropriately selected in such a way that the separation of the central internal axes of immediately adjacent catalyst tubes (known as the catalyst tube pitch) is from 35 to 45 mm (cf., for example, EP-B 468290).

Hourly space velocity on the fixed catalyst bed (here excluding pure inert sections) of reaction gas mixture in the process according to the invention will typically be from 1000 to 10 000 l (STP)/l·h, usually from 1000 to 5000 l (STP)/l·h, frequently from 1500 to 4000 l (STP)/l·h.

When the process according to the invention is performed, a fresh fixed catalyst bed, after it has been conditioned, will normally be operated in such a way that, after determining the composition of the reaction gas mixture and determining the hourly space velocity on the fixed catalyst bed of reaction gas mixture, the temperature of the fixed catalyst bed (or the inlet temperature of the heating medium into the heating zone of the tube bundle reactor) is adjusted in such a way that the conversion $C^{acr}$ of acrolein in single pass of the reaction gas mixture through the fixed catalyst bed is at least 90 mol %. When favorable catalysts are used, values for $C^{acr}$ of $\geq 92$ mol %, or $\geq 94$ mol %, or $\geq 96$ mol %, or $\geq 98$ mol %, and frequently even $\geq 99$ mol % and more are also possible.

When the heterogeneously catalyzed partial oxidation of acrolein to acrylic acid is performed continuously, the composition of the starting reaction gas mixture and the hourly space velocity on the fixed catalyst bed of starting reaction gas mixture will be kept substantially constant (if desired the hourly space velocity is adapted to the fluctuating market demand). A fall in the activity of the fixed catalyst bed over time will normally be counteracted under these production conditions by increasing the temperature of the fixed catalyst bed (the inlet temperature of the heating medium into the temperature zone of the tube bundle reactor) from time to time (the flow rate of the heating medium is likewise normally substantially retained), in order to keep the acrolein conversion in single pass of the reaction gas mixture within the desired target corridor (i.e. at values of $\geq 90$ mol %, or $\geq 92$ mol %, or $\geq 94$ mol %, or $\geq 96$ mol %, or $\geq 98$ mol %, or $\geq 99$ mol %). However, such a procedure is associated with the disadvantages described at the outset of this document.

The procedure will therefore, advantageously in accordance with the invention, be to interrupt the gas phase partial oxidation at least once before the temperature increase of the fixed catalyst bed which has been undertaken is permanently $\geq 10°$ C. or $\geq 8°$ C. (based on the temperature of the fixed catalyst bed set beforehand), in order to conduct an acrolein-free, oxidizing gas mixture G comprising molecular oxygen, inert gas and optionally steam and also optionally CO (consisting, for example, of molecular oxygen, inert gas and optionally steam) through the fixed catalyst bed at a temperature of the fixed catalyst bed of from 200 to 450° C. Subsequently, the partial oxidation is continued while substantially retaining the process conditions (preference is given to gradually reinstating the acrolein hourly space velocity on the fixed catalyst bed as in the case of a fresh, fixed catalyst bed, for example as described in DE-A 10337788) and the temperature of the fixed catalyst bed is adjusted in such a way that the acrolein conversion attains the desired target value. In general, this temperature value, for the same conversion, will be at a somewhat lower value than the temperature that the fixed catalyst bed had before the interruption of the partial oxidation and the inventive treatment with the gas mixture G. Starting from this temperature value of the fixed catalyst bed, the partial oxidation is continued while substantially retaining the remaining conditions, and the fall in the activity of the fixed catalyst bed over time is appropriately in turn counteracted by increasing the temperature of the fixed catalyst bed from time to time. Before the temperature increase of the fixed catalyst bed which has been carried out is permanently $\geq 10°$ C. or $\geq 8°$ C., the partial oxidation is, in accordance with the invention, in turn interrupted at least once, in order to conduct the gas mixture G through the fixed catalyst bed in the inventive manner. Afterward, the partial oxidation, advantageously in accordance with the invention, is started up again as described, etc.

The phrase "before the implemented temperature increase of the fixed catalyst bed is permanently $\geq 10°$ C. or $\geq 8°$ C. (generally $\geq X°$ C.)" takes into account that the temperature of the fixed catalyst bed on the industrial scale may undergo certain deviations for varying reasons. In this case, the actual profile of the temperature of the fixed catalyst bed is plotted over time and a fitted curve is drawn through the measurement points by the deviation of least squares method developed by Legendre and Gauss. When a temperature increase of $\geq 10°$ C. or $\geq 8°$ C. (generally of $\geq X°$ C.) is achieved on this fitted curve, the feature "permanent" is fulfilled.

It is surprising that in the long-term operation of heterogeneously catalyzed gas phase partial oxidation of acrolein to acrylic acid, the intensity of the hotspot expansion in the process according to the invention has more favorable behavior than in prior art processes. The process according to the invention thus enables on the one hand longer on-stream times of fixed catalyst bed in a reactor before it has to be partly or fully exchanged. On the other hand, the acrolein conversion achieved, integrated over time, is increased and the selectivity of acrylic acid formation is likewise promoted, since the location of the hotspot in the process according to the invention normally migrates over time in the direction of the inlet point of the reaction gas mixture into the fixed catalyst bed. The hotspot thus migrates in the reaction gas mixture increasingly into the region in which the acrylic acid content is still not very pronounced. This reduces the possibility that acrylic acid which has already formed undergoes partial undesired full combustion under the influence of the hotspot temperature. The hotspot temperature can be determined in the process according to the invention in tube bundle reactors, for example, by means of thermal tubes, as described in EP-A 873 783, WO 03-076373 and in EP-A 1 270 065. The number of such thermal tubes within a tube bundle reactor is appropriately from 4 to 20. Advantageously, they are arranged in uniform distribution within the tube bundle interior.

Frequently, the increase in the fixed catalyst bed temperature in the process according to the invention will be carried out in such a way that the acrolein conversion in single pass of the reaction gas mixture through the fixed catalyst bed does not go below 90 mol %, or 92 mol %, or 94 mol %, or 96 mol %, or 98 mol %, or 99 mol %. In other words, the fixed catalyst bed temperature will normally be increased at least once before 7500 or 7000, usually before 6000 and in many cases before 5000 or 4000, operating hours of the partial oxidation have been attained.

Finally, it should be emphasized that the increase in the fixed catalyst bed temperature over time in the process according to the invention when employing particularly favorable catalysts (for example that recommended in this document) is preferably carried out (usually substantially continuously and) in such a way that the acrolein content in the product gas mixture does not exceed the value of 1500 ppm by weight, preferably 600 ppm by weight and more preferably 350 ppm by weight. This takes into account that acrolein has a disruptive influence in the processes for removing acrylic acid from the product gas mixture of the partial oxidation in that it promotes the polymerization tendency of acrylic acid (cf. EP-A 1 041 062). In addition, the residual oxygen in the product gas mixture should generally be at least 1% by volume, preferably at least 2% by volume and more preferably at least 3% by volume.

The process according to the invention is especially advantageous where it is operated at an acrolein hourly space velocity on the fixed catalyst bed of $\geq 110$ l (STP)/l·h, or $\geq 120$ l (STP)/l·h, or 24 130 l (STP)/l·h. Generally, the freshly charged fixed catalyst bed will be configured in such a way that, as described in EP-A 990636 and in EP-A 1106598, both the hotspot development and its temperature sensitivity are very low. In addition, both in the case of first commissioning and in the case of recommissioning after the process according to the invention has been performed, the hourly space velocity on the fixed catalyst bed of acrolein will advantageously be left initially at values of $\leq 100$ l (STP)/l·h until stable operation has been established.

EXAMPLES

A) Preparation of the Catalyst Used

1. General Description of the Rotary Tube Furnace used for Calcination in the Preparation of Starting Compositions 1 and 2

Figure 1:
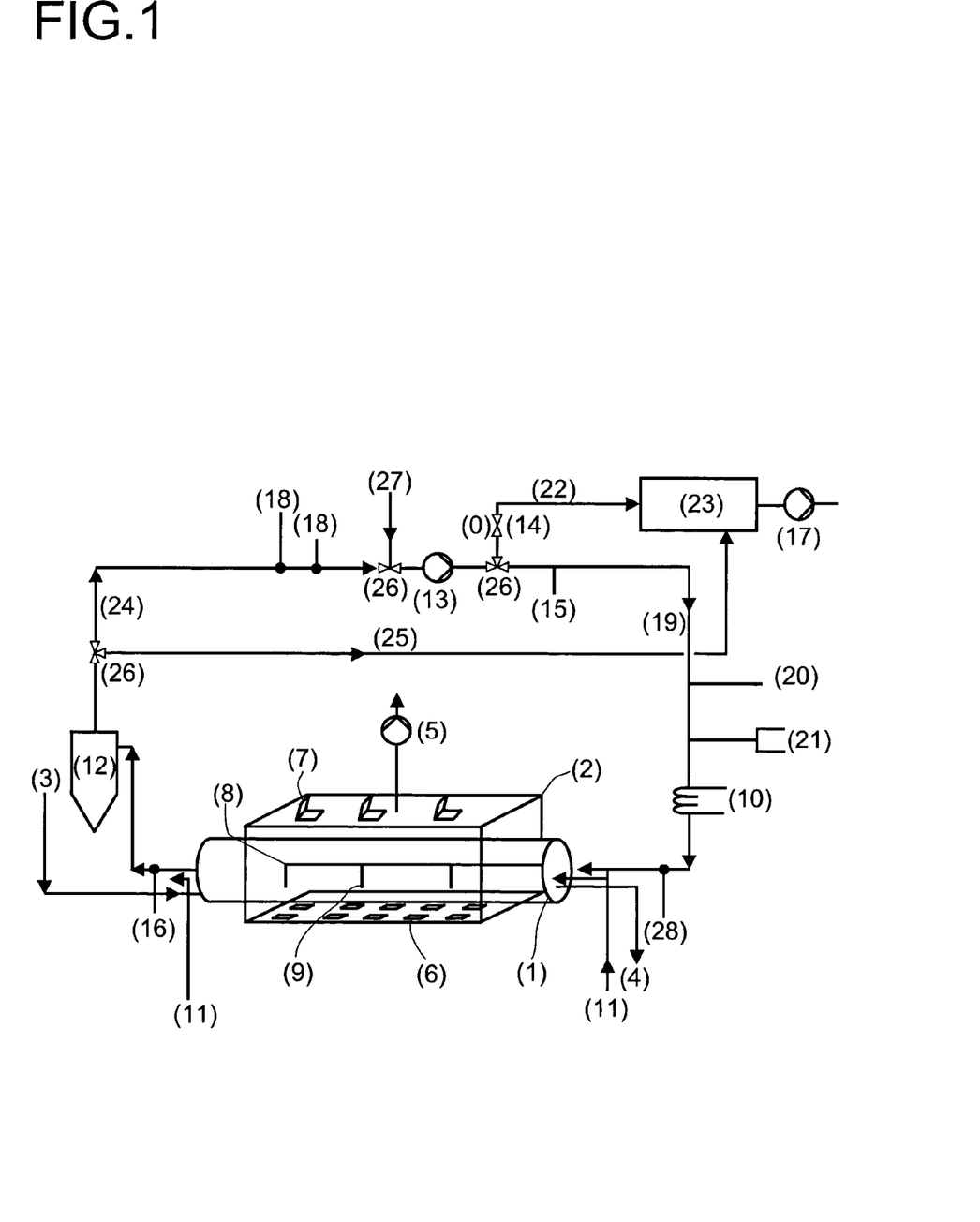
FIG. 1 shows a schematic diagram of a rotary tube furnace.

A schematic diagram of the rotary tube furnace is shown by the FIG. 1 appended to this document. The reference numerals which follow relate to this FIG. 1.

The central element of the rotary tube furnace is the rotary tube (1). It is 4000 mm long and has an internal diameter of 700 mm. It is manufactured from 1.4893 stainless steel and has a wall thickness of 10 mm.

On the interior wall of the rotary tube furnace are mounted lifting lances which have a height of 5 cm and a length of 23.5 cm. They primarily serve the purpose of lifting the material to be thermally treated in the rotary tube furnace, thus mixing it.

At one and the same height of the rotary tube furnace are mounted in each case four lifting lances (a quadruple) equidistantly around the circumference (separation in each case 90°). Along the rotary tube furnace are disposed eight such quadruples (each 23.5 cm apart). The lifting lances of two adjacent quadruples are offset relative to one another on the circumference. At the start and at the end of the rotary tube furnace (first and last 23.5 cm) there are no lifting lances.

The rotary tube rotates freely in a cuboid (2) which has four electrically heated (resistance heating) heating zones which are successive in the length of the rotary tube and are of equal length, each of which encloses the circumference of the rotary tube furnace. Each of the heating zones may heat the appropriate rotary tube section to temperatures between room temperature and 850° C. The maximum heating output of each heating zone is 30 kW. The distance between electrical heating zone and rotary tube exterior surface is about 10 cm. At the start and at the end, the rotary tube projects approx. 30 cm beyond the cuboid.

The rotation rate may be variably adjusted between 0 and 3 revolutions per minute. The rotary tube can be rotated either to the left or to the right. In the case of rotation to the right, the material remains in the rotary tube; in the case of rotation to the left, the material is conveyed from inlet (3) to outlet (4). The inclination angle of the rotary tube to the horizontal may be variably adjusted between 0° and 2°. In batchwise operation, it is in fact 0°. In continuous operation, the lowermost point of the rotary tube is at the material outlet. The rotary tube may be rapidly cooled by switching off the electrical heating zones and switching on a ventilator (5). This aspirates ambient air through holes (6) in the lower base of the cuboid, and conveys it through three flaps (7) having variably adjustable opening in the lid.

The material inlet is controlled via a rotary star feeder (mass control). The material output is, as already mentioned, controlled via the rotation direction of the rotary tube.

In the case of batchwise operation of the rotary tube, an amount of material of from 250 to 500 kg may be thermally treated. The amount is normally disposed exclusively in the heated section of the rotary tube.

From a lance (8) lying on the central axis of the rotary tube, a total of three thermal elements (9) lead vertically into the material at intervals of 800 mm. They enable the determination of the temperature of the material. In this document, temperature of the material refers to the arithmetic mean of the three thermal element temperatures. According to the invention, the maximum deviation of two measured temperatures within the material in the rotary tube is appropriately less than 30° C., preferably less than 20° C., more preferably less than 10° C. and most preferably less than 5 or 3° C.

Gas streams may be conducted through the rotary tube, by means of which the calcination atmosphere or generally the atmosphere of the thermal treatment of the material can be adjusted.

The heater (10) offers the possibility of heating the gas stream conducted into the rotary tube to the desired temperature before its entry into the rotary tube (for example to the temperature desired in the rotary tube for the material). The maximum output of the heater is 1×50 kW+1×30 kW. In principle, the heater (10) may be, for example, an indirect heat exchanger. Such a heater may in principle also be used as a cooler. However, it is generally an electrical heater in which the gas stream is conducted over metal wires heated using electricity (appropriately a 97D/80 CSN flow heater from C. Schniewindt KG, 58805 Neuerade, Germany).

In principle, the rotary tube apparatus provides the possibility of partly or fully recycling the gas stream conducted through the rotary tube. The recycle line required for this purpose is connected to the rotary tube in a mobile manner at the rotary tube inlet and at the rotary tube outlet using ball bearings or using graphite pressure seals. These connections are flushed with inert gas (e.g. nitrogen) (barrier gas). The two flush streams (11) supplement the gas stream conducted through the rotary tube at the inlet into the rotary tube and at the outlet from the rotary tube. Appropriately, the rotary tube narrows at its start and at its end and projects into the tube of the recycle line leading to and away from it respectively.

Downstream of the outlet of the gas stream conducted through the rotary tube is disposed a cyclone (12) to remove solid particles entrained with the gas stream (the centrifugal separator separates solid particles suspended in the gas phase by interaction of centrifugal force and gravity; the centrifugal force of the gas stream rotating as a spiral accelerates the sedimentation of the suspended particles).

The conveying of the cycle gas stream (24) (the gas circulation) is effected by means of a cycle gas compressor (13) (ventilator) which aspirates in the direction of the cyclone and forces in the other direction. Directly downstream of the cycle gas compressor, the gas pressure is generally above one atmosphere. Downstream of the cycle gas compressor is disposed a cycle gas outlet (cycle gas may be discharged via a regulating valve (14)). A diaphragm disposed downstream of the outlet (cross-sectional reduction by about a factor of 3, pressure reducer) (15) eases the discharge.

The pressure downstream of the rotary tube outlet can be controlled via the regulating valve. This is effected in combination with a pressure sensor (16) mounted downstream of the rotary tube outlet, the offgas compressor (17) (ventilator) which aspirates toward the regulating valve, the cycle gas compressor (13) and the fresh gas feed. Relative to the external pressure, the pressure (directly) downstream of the rotary tube outlet may be set, for example, to up to +1.0 mbar higher and, for example, up to −1.2 mbar lower. In other words, the pressure of the gas stream flowing through the rotary tube may be below the ambient pressure of the rotary tube when it leaves the rotary tube.

When the intention is not to at least partly recycle the gas stream conducted through the rotary tube, the connection between cyclone (12) and cycle gas compressor (13) is made by the three-way valve principle (26) and the gas stream is conducted directly into the offgas cleaning apparatus (23).

The connection to the offgas cleaning apparatus disposed downstream of the cycle gas compressor is in this case likewise made by the three-way valve principle. When the gas stream consists substantially of air, it is in this case aspirated (27) via the cycle gas compressor (13). The connection to the cyclone is made by the three-way valve principle. In this case, the gas stream is preferably sucked through the rotary tube, so that the internal rotary tube pressure is less than the ambient pressure.

In the case of continuous operation of the rotary tube furnace apparatus, the pressure downstream of the rotary tube outlet is advantageously set −0.2 mbar below the external pressure. In the case of batchwise operation of the rotary tube apparatus, the pressure downstream of the rotary tube outlet is advantageously set −0.8 mbar below the external pressure. The slightly reduced pressure serves the purpose of preventing contamination of the ambient air with gas mixture from the rotary tube furnace.

Between the cycle gas compressor and the cyclone are disposed sensors (18) which determine, for example, the ammonia content and the oxygen content in the cycle gas. The ammonia sensor preferably operates by an optical measurement principle (the absorption of light of a certain wavelength correlates proportionally to the ammonia content of the gas) and is appropriately an MCS 100 instrument from Perkin & Elmer. The oxygen sensor is based on the paramagnetic properties of oxygen and is appropriately an Oximat from Siemens of the Oxymat MAT SF 7MB1010-2CA01-1AA1-Z type.

Between the diaphragm (15) and the heater (10), gases such as air, nitrogen, ammonia or other gases may be metered into the cycle gas fraction (19) which has actually been recirculated. Frequently, a base load of nitrogen is metered in (20). A separate nitrogen/air splitter (21) may be used to react to the measurement of the oxygen sensor.

The discharged cycle gas fraction (22) (offgas) frequently contains gases such as $NO_x$, acetic acid, $NH_3$, etc. which are not completely safe, which is why they are normally removed in an offgas cleaning apparatus (23).

To this end, the offgas is generally initially conducted through a washing column (essentially a column free of internals which contains a separating structured packing upstream of its outlet; the offgas and aqueous sprayed mist are conducted in countercurrent and in cocurrent (2 spray nozzles having opposite spray direction).

Exiting the washing column, the offgas is conducted into an apparatus which contains a fine dust filter (generally a series of bag filters) from whose interior the penetrant offgas is discharged. Finally, incineration is effected in a muffle furnace.

A sensor (28) from KURZ Instruments, Inc., Montery (USA) of the 455 Jr model is used to measure and control the flow rate of the gas stream which is fed to the rotary tube and is different to the barrier gas (measurement principle: thermal-convective mass flow measurement using an isothermal anemometer).

In the case of continuous operation, material and gas phase are conducted through the rotary tube furnace in countercurrent.

In connection with this example, nitrogen always means nitrogen having a purity of >99% by volume.

2. Preparation of the Starting Composition 1 (phase B) having the Stoichiometry $Cu_1Mo_{0.5}W_{0.5}O_4$ 98 l of a 25% by weight aqueous $NH_3$ solution were added to 603 l of water. Subsequently, 100 kg of copper(II) acetate hydrate (content: 40.0% by weight of CuO) were dissolved in the aqueous mixture to give a clear, deep blue aqueous solution 1 which contained 3.9% by weight of Cu and was at room temperature.

Independently of the solution 1, 620 l of water were heated to 40° C. 27.4 kg of ammonium heptamolybdate tetrahydrate (81.5% by weight of $MoO_3$) were dissolved therein with stirring within 20 min while maintaining the 40° C. 40.4 kg of ammonium paratungstate heptahydrate (88.9% by weight of $WO_3$) were then added and, after heating to 90° C., dissolved with stirring at this temperature within 45 min. A clear, yellow-orange-colored aqueous solution 2 was obtained.

Subsequently, the aqueous solution 1 was stirred into the solution 2 at 90° C., in the course of which the temperature of the overall mixture did not fall below 80° C. The resulting aqueous suspension was stirred at 80° C. for 30 min. Afterward, it was spray-dried using an S-50-N/R spray dryer from Niro-Atomizer (Copenhagen) (gas inlet temperature: 315° C., gas outlet temperature: 110° C., cocurrent). The spray powder had a particle diameter of from 2 to 50 µm.

100 kg of light green spray powder obtained in this way were metered into a VIU 160 kneader (Sigma blades) from AMK (Aachener Misch- und Knetmaschinen Fabrik) and kneaded with the addition of 8 l of water (residence time: 30 min, temperature: 40 to 50° C.). Afterward, the kneaded material was emptied into an extruder and shaped to extrudates (length: 1–10 cm; diameter: 6 mm) by means of the extruder (from Bonnot Company (Ohio), type: G 103-10/D7A-572K (6" Extruder W/Packer)). On a belt dryer, the extrudates were dried at a temperature of 120° C. (material temperature) for 1 h. The dried extrudates were subsequently thermally treated (calcined) in the rotary tube furnace described under "1." as follows:

the thermal treatment was effected continuously with a material input of 50 kg/h of extrudates;

the inclination angle of the rotary tube to the horizontal was 2°;

in countercurrent to the material, an air stream of 75 m³ (STP)/h was conducted through the rotary tube and was supplemented by a total of (2×25) 50 m³ (STP)/h of barrier gas at 25° C.;

the pressure downstream of the rotary tube outlet was 0.8 mbar below the external pressure;

the rotary tube rotated to the left at 1.5 revolutions/min;

no cycle gas method was employed;

in the first pass of the extrudates through the rotary tube, the temperature of the external rotary tube wall was set to 340° C.; the air stream was conducted into the rotary tube at a temperature of from 20 to 30° C.;

subsequently, the extrudates were conducted through the rotary tube at the same throughput rate and under the same conditions, apart from the following differences:

the temperature of the rotary tube wall was set to 790° C.;

the air stream was conducted into the rotary tube heated to a temperature of 400° C.

Subsequently, the extrudates having a red-brown color were ground to an average particle diameter of from 3 to 5 µm on a BQ 500 Biplex cross flow classifying mill from Hosokawa-Alpine (Augsburg). The starting composition 1 obtained in this way had a BET surface area of $\leq 1$ m²/g. X-ray diffraction was used to determine the following phases:

1. $CuMoO_4$-III having wolframite structure;
2. HT copper molybdate.

3. Preparation of the Starting Composition 2 (Phase C) having the Stoichiometry $CuSb_2O_6$ 52 kg of antimony trioxide (99.9% by weight of $Sb_2O_3$) were suspended with stirring in 216 l of water (25° C.). The resulting aqueous suspension was heated to 80° C. Subsequently, stirring was continued while maintaining the 80° C. for 20 min. Subsequently, 40 kg of a 30% by weight aqueous hydrogen peroxide solution were added within one hour, in the course of which the 80° C. were maintained. While maintaining this temperature, stirring was continued for 1.5 hours. 20 l of water at 60° C. were then added to obtain an aqueous suspension 1.618.3 kg of an aqueous ammoniacal copper(II) acetate solution (60.8 g of copper acetate per kg of solution and 75 l of a 25% by weight aqueous ammonia solution in the 618.3 kg of solution) were stirred into this solution at a temperature of 70° C. The mixture was then heated to 95° C. and stirring was continued at this temperature for 30 min. Another 50 l of water at 70° C. were then added and the mixture was heated to 80° C.

Finally, the aqueous suspension was spray-dried (S-50-N/R spray dryer from Niro-Atomizer (Copenhagen), gas inlet temperature 360° C., gas outlet temperature 110° C., cocurrent). The spray powder had a particle diameter of from 2 to 50 μm.

75 kg of the spray powder obtained in this way were metered into a VIU 160 kneader (Sigma blades) from AMK (Aachener Misch- und Knetmaschinen Fabrik) and kneaded with the addition of 12 l of water (residence time: 30 min, temperature from 40 to 50° C.). Afterward, the kneaded material was emptied into an extruder (same extruder as in phase B preparation) and shaped to extrudates (length 1-10 cm; diameter 6 mm) using the extruder. On a belt dryer, the extrudates were dried at a temperature of 120° C. (material temperature) for 1 h.

250 kg of extrudates obtained in this way were thermally treated (calcined) in the rotary tube furnace described under "1." as follows:
- the thermal treatment was effected batchwise with a material amount of 250 kg;
- the inclination angle of the rotary tube to the horizontal was≈0°;
- the rotary tube rotated to the right at 1.5 revolutions/min;
- a gas stream of 205 m³ (STP)/h was conducted through the rotary tube; at the start of the thermal treatment, this consisted of 180 m³ (STP)/h of air and 1×25 m³ (STP)/h of $N_2$ as barrier gas; the gas stream leaving the rotary tube was supplemented by a further 1×25 m³ (STP)/h of $N_2$; of this overall stream, 22-25% by volume was recycled into the rotary tube and the remainder discharged; the discharge amount was supplemented by the barrier gas and the remainder by fresh air;
- the gas stream was conducted into the rotary tube at 25° C.;
- the pressure downstream of the rotary tube outlet was 0.5 mbar below external pressure (atmospheric pressure);
- the temperature in the material was initially increased linearly from 25° C. to 250° C. within 1.5 h; the temperature in the material was then increased linearly from 250° C. to 300° C. within 2 h and this temperature was maintained for 2 h; then the temperature in the material was increased linearly from 300° C. to 405° C. within 3 h and this temperature was subsequently maintained for 2 h; the heating zones were then switched off and the temperature within the material was reduced to a temperature below 100° C. within 1 h by activating the rapid cooling of the rotary tube by aspirating air and finally cooled to ambient temperature.

The resulting pulverulent starting composition 2 had a specific BET surface area of 0.6 m²/g and the composition $CuSb_2O_6$. The powder x-ray diagram of the resulting powder showed substantially the refraction angles of $CuSb_2O_6$ (comparative spectrum 17-0284 of the JCPDS-ICDD index).

4. Preparation of the Starting Composition 3 having the Stoichiometry $Mo_{12}V_{3.35}W_{1.38}$ A stirred tank was initially charged with 900 l of water at 25° C. with stirring. Subsequently, 122.4 kg of ammonium heptamolybdate tetrahydrate (81.5% by weight of $MoO_3$) were added and the mixture was heated to 90° C. with stirring. Initially 22.7 kg of ammonium metavanadate and finally 20.0 kg of ammonium paratungstate heptahydrate (88.9% by weight of $WO_3$) were then stirred in while maintaining the 90° C. Stirring at 90° C. for a total of 80 minutes resulted in a clear orange-colored solution. This was cooled to 80° C. While maintaining the 80° C., initially 18.8 kg of acetic acid (≈100% by weight, glacial acetic acid) and then 24 l of 25% by weight aqueous ammonia solution were then stirred in.

The solution remained clear and orange-colored and was spray-dried using an S-50-N/R spray dryer from Niro-Atomizer (Copenhagen) (gas inlet temperature: 260° C., gas outlet temperature: 110° C., cocurrent). The resulting spray powder formed the starting composition 3 and had a particle diameter of from 2 to 50 μm.

5. Preparation of the Dry Composition to be Treated Thermally and having the Stoichiometry $(Mo_{12}V_{3.46}W_{1.39})_{0.87}$ $(CuMo_{0.5}W_{0.5}O_4)_{0.4}$ $(CuSb_2O_6)_{0.4}$ In a VIU 160 trough kneader having two Sigma blades from AMK (Aachener Mischund Knetmaschinen Fabrik), 75 kg of starting composition 3, 5.2 l of water and 6.9 kg of acetic acid (100% by weight glacial acetic acid) were initially charged and kneaded over 22 min. Subsequently, 3.1 kg of starting composition 1 and 4.7 kg of starting composition 2 were added and kneaded over a further 8 min (T≈40 to 50° C.).

Afterward, the kneaded material was emptied into an extruder (same extruder as in phase B preparation) and shaped to extrudates (length from 1 to 10 cm, diameter 6 mm) using the extruder. These were then dried at a temperature (material temperature) of 120° C. over 1 h on a belt dryer.

306 kg of the dried extrudates were subsequently thermally treated in the rotary tube furnace described under "1." as follows:
- the thermal treatment was effected batchwise with a material amount of 306 kg;
- the inclination angle of the rotary tube to the horizontal was≈0°;
- the rotary tube rotated to the right at 1.5 revolutions/min;
- initially, the material temperature was increased substantially linearly from 25° C. to 100° C. within 2 h;
- during this time, a (substantially) nitrogen stream of 205 m³ (STP)/h is fed through the rotary tube. In the steady state (after displacement of air which was originally present), this has the following composition:
  110 m³ (STP)/h of baseload nitrogen (20),
  25 m³ (STP)/h of barrier gas nitrogen (11), and
  70 m³ (STP)/h of recirculated cycle gas (19).
The barrier gas nitrogen was fed at a temperature of 25° C. . The mixture of the two other nitrogen streams was conducted into the rotary tube in each case at the temperature that the material had in each case in the rotary tube.

subsequently, the material temperature was increased from 100° C. to 320° C. at a heating rate of 0.7° C./min; until a material temperature of 300° C. had been attained, a gas stream of 205 m³ (STP)/h was conducted through the rotary tube and had the following composition:
110 m³ (STP)/h consisting of baseload nitrogen (20) and gases released in the rotary tube,
25 m³ (STP)/h of barrier gas nitrogen (11) and
70 m³ (STP)/h of recirculated cycle gas (19).

The barrier gas nitrogen was fed at a temperature of 25° C. The mixture of the two other gas streams was conducted into the rotary tube in each case at the temperature that the material had in each case in the rotary tube.

From the exceedance of the material temperature of 160° C. to the attainment of a material temperature of 300° C., 40 mol % of the total amount of ammonia $M^A$ released in the course of the overall thermal treatment of the material was released from the material.

on attainment of the material temperature of 320° C., the oxygen content of the gas stream fed to the rotary tube was increased from 0% by volume to 1.5% by volume and maintained over the following 4 h.

At the same time, the temperature in the four heating zones heating the rotary tube was reduced by 5° C. (to 325° C.) and maintained thus over the following 4 h.

The material temperature passed through a temperature maximum above 325° C. which did not exceed 340° C. before the material temperature fell back to 325° C.

The composition of the gas stream conducted through the rotary tube of 205 m³ (STP)/h was changed as follows over this period of 4 h:
95 m³ (STP)/h consisting of baseload nitrogen (20) and gases released in the rotary tube;
25 m³ (STP)/h of barrier gas nitrogen (11);
70 m³ (STP)/h of recirculated cycle gas; and
15 m³ (STP)/h of air via the splitter (21).

The barrier gas nitrogen was fed at a temperature of 25° C.

The mixture of the other gas streams was in each case conducted into the rotary tube at the temperature that the material had in each case in the rotary tube.

From the exceeding of the material temperature of 300° C. until the 4 h had elapsed, 55 mol % of the total amount of ammonia released $M^A$ in the course of the overall thermal treatment of the material was released from the material (a total of 40 mol %+55 mol %=95 mol % of the amount of ammonia $M^A$ had thus been released before 4 h had elapsed).

when the 4 h had elapsed, the temperature of the material was increased to 400° C. within about 1.5 h at a heating rate of 0.85° C./min.

Subsequently, this temperature was maintained for 30 min.

The composition of the gas stream fed to the rotary tube of 205 m³ (STP)/h over this time was as follows:
95 m³ (STP)/h composed of baseload nitrogen (20) and gases released in the rotary tube;
15 m³ (STP)/h of air (splitter (21));
25 m³ (STP)/h of barrier gas nitrogen (11); and
70 m³ (STP)/h of recirculated cycle gas.

The barrier gas nitrogen was fed at a temperature of 25° C. The mixture of the other gas streams was in each case conducted into the rotary tube at the temperature that the material had in each case in the rotary tube.

reducing the temperature of the material ended the calcination; to this end, the heating zones were switched off and the rapid cooling of the rotary tube by aspirating air was switched on, and the material temperature was reduced to a temperature below 100° C. within 2 h and finally cooled to ambient temperature;

with the switching-off of the heating zones, the composition of the gas stream fed to the rotary tube of 205 m³ (STP)/h was changed to the following mixture:
110 m³ (STP)/h composed of baseload nitrogen (20) and gases released in the rotary tube;
0 m³ (STP)/h of air (splitter (21));
25 m³ (STP)/h of barrier gas nitrogen (11); and
70 m³ (STP)/h of recirculated cycle gas.

The gas stream was fed to the rotary tube at a temperature of 25° C.

over the entire thermal treatment, the pressure (immediately) downstream of the rotary tube outlet was 0.2 mbar below the external pressure.

6. Shaping of the Multimetal Oxide Active Composition

The catalytically active material obtained in "5." was ground using a BQ 500 Biplex cross flow classifying mill (Hosokawa-Alpine Augsburg) to a finely divided powder of which 50% of the powder particles passed through a sieve of mesh width from 1 to 10 μm and whose fraction of particles having a largest dimension above 50 μm was less than 1%.

The ground powder was used as in S1 of EP-B 714700 to coat annular support bodies (external diameter 7 mm, length 3 mm, internal diameter 4 mm, steatite of the type C220 from CeramTec having a surface roughness Rz of 45 μm). The binder was an aqueous solution of 75% by weight of water and 25% by weight of glycerol.

However, the selected active composition fraction of the resulting coated catalysts was, in contrast to the aforementioned example S1, 20% by weight (based on the total weight of support body and active composition). The ratio of powder and binder was adapted proportionately.

Figure 2:
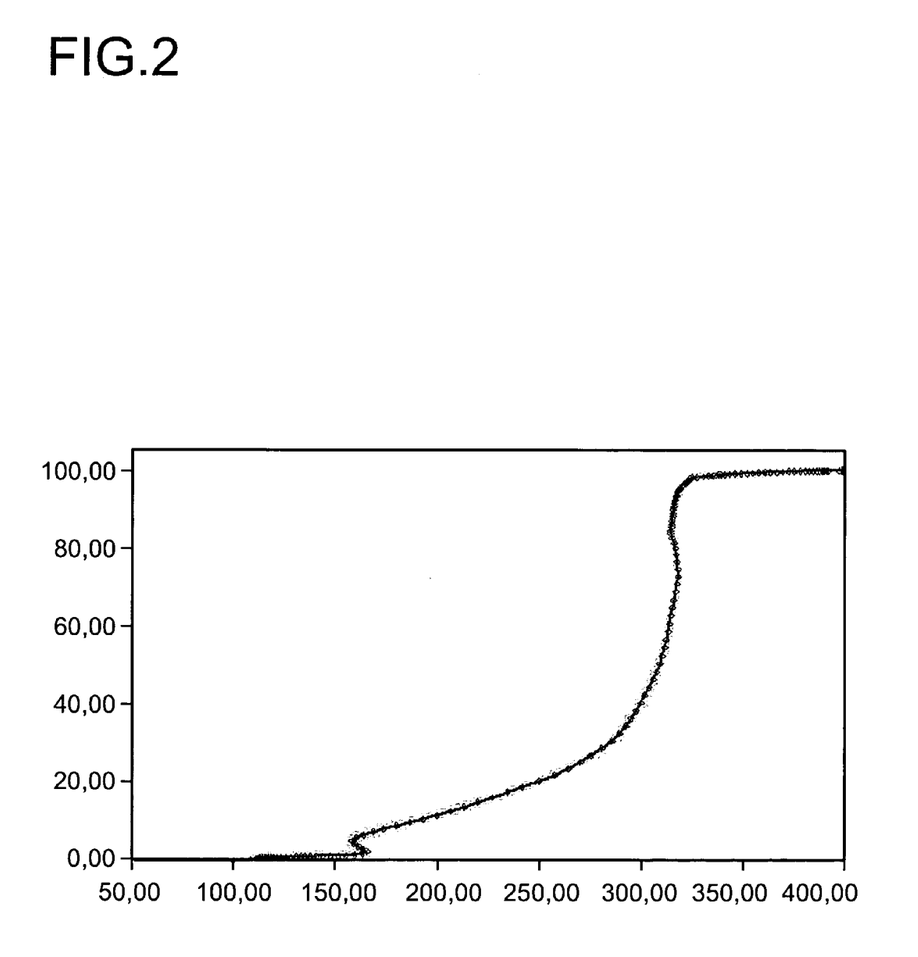
FIG. 2 shows the percentage of $M^4$ as a function of the material temperature in ° C.
Figure 3:
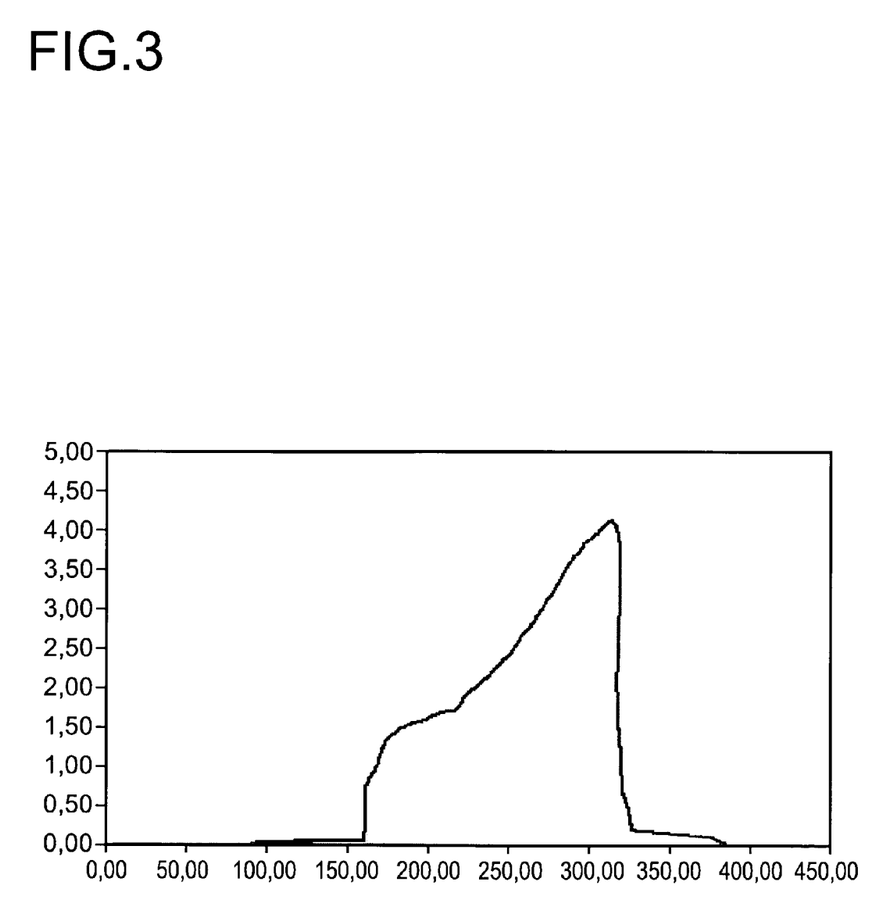
FIG. 3 shows the ammonia concentration of the atmosphere A in % by volume over the thermal treatment as a function of the material temperature in ° C.

FIG. 2 shows the percentage of $M^A$ as a function of the material temperature in ° C. FIG. 3 shows the ammonia concentration of the atmosphere A in % by volume over the thermal treatment as a function of the material temperature in ° C.

B) Performance of the Partial Oxidation

I. Description of the General Process Conditions

| | |
|---|---|
| Heat exchange medium used: | Salt melt consisting of 60% by weight of potassium nitrate and 40% by weight of sodium nitrite |
| Material of the catalyst tubes: | ferritic steel |
| Dimensions of the catalyst tubes: | Length 3200 mm; internal diameter 25 mm; external diameter 30 mm (wall thickness: 2.5 mm) |
| Number of catalyst tubes in the tube bundle: | 25 500 |
| Reactor: | Cylindrical vessel of diameter 6800 mm; annularly arranged tube bundle having a free central space. Diameter of the central free space: 1000 mm. Distance of the outermost catalyst tubes from the vessel wall: 150 mm. |

| | -continued |
|---|---|
| Catalyst tube pitch: | Homogeneous catalyst tube distribution in the tube bundle (6 equidistant neighboring tubes per catalyst tube). 38 mm. |

The catalyst tubes were secured and sealed by their ends in catalyst tube plates of thickness 125 mm and opened with their orifices each into a hood connected to the vessel at the upper or lower end.

Feed of the heat exchange medium to the tube bundle:

The tube bundle was divided by three deflecting plates (thickness in each case 10 mm) mounted in succession between the catalyst tube plates in the longitudinal direction into 4 equidistant (each 730 mm) longitudinal sections (zones).

The uppermost and the lowermost deflecting plate had annular geometry, the internal annular diameter was 1000 mm and the external annular diameter extended with sealing to the vessel wall. The catalyst tubes were not secured and sealed to the deflecting plates. Rather, a gap having a gap width of <0.5 mm was left in such a way that the transverse flow rate of the salt melt was substantially constant within one zone.

The middle deflecting plate was circular and extended up to the outermost catalyst tubes of the tube bundle.

The recycling of the salt melt was brought about by two salt pumps, each of which supplied one longitudinal half of the tube bundle.

The pumps compressed the salt melt into an annular channel which was arranged at the bottom around the reactor jacket and divided the salt melt over the vessel circumference. The salt melt reached the tube bundle in the lowermost longitudinal section through windows in the reactor jacket. The salt melt then flowed as dictated by the deflecting plates in the sequence    from the outside inward,
   from the inside outward,
   from the outside inward,
   from the inside outward, in a substantially meandering manner, viewed over the vessel, from bottom to top. The salt melt collected through windows mounted in the uppermost longitudinal section around the vessel circumference in an annular channel mounted at the top around the reactor jacket and, after cooling to the original inlet temperature, was compressed back into the lower annular channel by the pumps.

The composition of the starting reaction gas mixture was within the following framework over the operating time:

from 4 to 6% by volume of acrolein,
   from 5 to 8% by volume of $O_2$,
   from 1.2 to 2.5% by volume of $CO_x$,
   from 6 to 10% by volume of $H_2O$ and
   at least 75% by volume of $N_2$.

| | |
|---|---|
| Reactor charge: | Salt melt and reaction gas mixture were conducted in countercurrent viewed over the reactor. The salt melt entered from the bottom, the reaction gas mixture from the top.<br>The inlet temperature of the salt melt at the start (on completion of conditioning of the fixed catalyst bed) was approx. 265° C. The associated outlet temperature of the salt |

| | -continued |
|---|---|
| | melt at the start was approx. 267° C.<br>The pump output was 6200 m³ of salt melt/h.<br>The starting reaction gas mixture was fed to the reactor at a temperature of 240° C. |
| Acrolein loading of the fixed catalyst bed: | from 95 to 110 l (STP)/l · h |
| The catalyst tube charge with fixed catalyst bed (from top to bottom) was: | Zone A:<br>20 cm preliminary bed of steatite rings of geometry 7 mm × 7 mm × 4 mm (external diameter × length × internal diameter).<br>Zone B:<br>100 cm catalyst charge of a homogeneous mixture of 30% by weight of steatite rings of geometry 7 mm × 3 mm × 4 mm (external diameter × length × internal diameter) and 70% by weight of the annular (approx. 7 mm × 3 mm × 4 mm) coated catalyst prepared.<br>Zone C:<br>200 cm catalyst charge of the annular (approx. 7 mm × 3 mm × 4 mm) coated catalyst prepared. |

The thermal tubes (their number was 10 which were uniformly distributed in the central region of the tube bundle) were configured and charged as follows:

(they were used to determine the hotspot temperature; this is an arithmetic average of independent measurements in the 10 thermal tubes)

Each of the 10 thermal tubes had a central thermowell having 40 temperature measurement points (i.e. each thermal tube contained 40 thermoelements which were integrated into a thermowell at different lengths and thus formed a multithermoelement by which the temperature could be simultaneously determined within the thermal tube at different heights).

At least 13 and at most 30 of the in each case 40 temperature measurement points were in the region of the first meter of the active section of the fixed catalyst bed (in the flow direction of the reaction gas mixture).

The internal diameter of a thermal tube was 27 mm. The wall thickness and tube material were as in the working tubes.

The external diameter of the thermowell was 4 mm.

A thermal tube was charged with the annular coated catalyst prepared. In addition, spherical coated catalyst (same active composition as the annular coated catalyst, the diameter of the Steatite C220 (CeramTec) support spheres was 2–3 mm; the active composition fraction was 20% by weight, the preparation was as described for the annular coated catalyst, except that the binder was an appropriate amount of water) was charged into the thermal tube.

The spherical coated catalyst was charged in homogeneous distribution over the entire active section of the fixed catalyst bed of the particular thermal tube, in such a way that the pressure drop of the reaction gas mixture as it passed through the thermal tube corresponded to that when the reaction gas mixture passed through a working tube (based on the active section of the fixed catalyst bed (i.e. excluding the inert sections); for this purpose, from 5 to 20% by weight of spherical coated catalyst were required in the thermal tube). At the same time, the particular total fill height of active and inert sections in the working and thermal tubes was the same and the ratio of the total amount of active composition present in the tube to heat exchange surface area of the tube in working and thermal tubes set to the same value.

II. Long-Term Operation (Results)

The target conversion for the acrolein to be converted in single pass of the reaction gas mixture through the fixed catalyst bed was set at 99.3 mol %.

Successive increases in the inlet temperature of the salt melt allowed this conversion value to be maintained over time when the process was carried out continuously. Once per calendar month, the partial oxidation was interrupted (the increase in the inlet temperature of the salt melt up to the monthly interruption was always $\geq 0.3°$ C. and $\leq 4°$ C.), the inlet temperature of the salt melt which was last employed was retained and a gas mixture G was conducted through the fixed catalyst bed at an hourly space velocity on the fixed catalyst bed of 30 l (STP)/l·h for a period $t_G$ of from 24 h to 48 h. The oxygen content of the gas mixture G was increased in the course of the period $t_G$ from approx. 2% by volume to 6% by volume. The CO and the $CO_2$ content of the gas mixture G were reduced in the course of the period $t_G$ from values of $\leq 1\%$ by volume (CO) and $\leq 4\%$ by volume ($CO_2$) to 0% by volume, the steam content was $\leq 6\%$ by volume, the content of molybdenum oxide hydrate was $\leq 1$ ppm by weight and the remainder of the gas mixture G consisted substantially of nitrogen.

The partial oxidation was then continued and the inlet temperature of the salt melt was adjusted in such a way that the target conversion was still attained.

The inlet temperature of the salt melt and the hotspot temperature and also the selectivity $S^{AA}$ of acrylic acid formation developed as follows:

| Start: | Salt melt inlet temperature = | 265° C. |
|---|---|---|
| | Hotspot temperature = | 290° C. |
| | $S^{AA}$ = | 94.3 mol % |
| After 1 year of operating time: | Salt melt inlet temperature = | 276° C. |
| | Hotspot temperature = | 297° C. |
| | $S^{AA}$ = | 94.2 mol % |
| After 2 years of operating time: | Salt melt inlet temperature = | 282° C. |
| | Hotspot temperature = | 303° C. |
| | $S^{AA}$ = | 94.3 mol % |
| After 3 years of operating time: | Salt melt inlet temperature = | 299° C. |
| | Hotspot temperature = | 312° C. |
| | $S^{AA}$ = | 94.4 mol % |

Within the 3 years of operating time, the location of the hotspot temperature migrated by approx. 25 cm in the direction of the inlet point of the reaction gas mixture.

In a second identically designed and identically charged and also operated tube bundle reactor, the partial oxidation was carried out in a corresponding manner and the following results were obtained:

| Start: | Salt melt inlet temperature = | 266° C. |
|---|---|---|
| | Hotspot temperature = | 292° C. |
| | $S^{AA}$ = | 94.6 mol % |
| After 1 year of operating time: | Salt melt inlet temperature = | 274° C. |
| | Hotspot temperature = | 299° C. |
| | $S^{AA}$ = | 94.6 mol % |
| After 2 years of operating time: | Salt melt inlet temperature = | 283° C. |
| | Hotspot temperature = | 305° C. |
| | $S^{AA}$ = | 94.7 mol % |
| After 3 years of operating time: | Salt melt inlet temperature = | 299° C. |
| | Hotspot temperature = | 311° C. |
| | $S^{AA}$ = | 94.7 mol % |

The migration of the location of the hotspot temperature was as above.

The temperature data (apart from the start) relate in all cases to the time in each case which was just before the interruption of the partial oxidation and the treatment of the fixed catalyst bed with the gas mixture G.

U.S. Provisional Patent Application No. 60/514,918, filed on Oct. 29, 2003, is incorporated into the present application by literature reference.

With reference to the abovementioned teachings, numerous alterations and deviations from the present invention are possible. It may therefore be assumed that the invention within the scope of the appended claims, may be performed differently from the way specifically described herein.

We claim:

1. A process for the long-term operation of a heterogeneously catalyzed gas phase partial oxidation of acrolein to acrylic acid, by conducting a starting reaction gas mixture which comprises acrolein, molecular oxygen and at least one inert diluent gas through a fixed catalyst bed at elevated temperature whose catalysts are such that their active composition is at least one multimetal oxide which contains the elements Mo and V, and by, in order to counteract the deactivation of the fixed catalyst bed, increasing the temperature of the fixed catalyst bed over time, which comprises interrupting the gas phase partial oxidation at least once before the temperature increase of the fixed catalyst bed is permanently $\geq 10°$ C., and, at a temperature of the fixed catalyst bed of from 200 to 450° C., conducting an acrolein-free, oxidizing gas mixture G comprising molecular oxygen, inert gas and optionally steam and also optionally CO through the fixed catalyst bed.

2. A process as claimed in claim 1, wherein the gas phase partial oxidation is interrupted at least once before the temperature increase of the fixed catalyst bed is permanently $\geq 8°$ C. and the gas mixture G is conducted through the fixed catalyst bed.

3. A process as claimed in claim 1, wherein the gas phase partial oxidation is interrupted at least once before the temperature increase of the fixed catalyst bed is permanently $\geq 4°$ C. and the gas mixture G is conducted through the fixed catalyst bed.

4. A process as claimed in claim 1, wherein the gas phase partial oxidation is interrupted at least once before the temperature increase of the fixed catalyst bed is permanently $\geq 2°$ C. and the gas mixture G is conducted through the fixed catalyst bed.

5. A process as claimed in claim 1, wherein the duration over which the gas mixture G is conducted through the fixed catalyst bed is from 2 h to 120 h.

6. A process as claimed in claim 1, wherein the gas mixture G which is conducted through the fixed catalyst bed contains at least 2% by volume of oxygen.

7. A process as claimed in claim 1, wherein the gas mixture G which is conducted through the fixed catalyst bed contains at least 3% by volume of oxygen.

8. A process as claimed in claim 1, wherein the gas mixture G which is conducted through the fixed catalyst bed contains from 1 to 8% by volume of oxygen, from 0 to 3% by volume of CO, from 0 to 5% by volume of $CO_2$, from 0 to 25% by volume of $H_2O$ and at least 55% by volume of $N_2$.

9. A process as claimed in claim 1, wherein the active composition of the catalysts is at least one multimetal oxide of the general formula I (I)

in which the variables are each defined as follows:
$X^1$=W, Nb, Ta, Cr and/or Ce,
$X^2$=Cu, Ni, Co, Fe, Mn and/or Zn,
$X^3$=Sb and/or Bi,
$X^4$=one or more alkali metals,
$X^5$=one or more alkaline earth metals,
$X^6$=Si, Al, Ti and/or Zr,
a=from 1 to 6,
b=from 0.2 to 4,
c=from 0.5 to 18,
d=from 0 to 40,
e=from 0 to 2,
f=from 0 to 4,
g=from 0 to 40 and
n=a number which is determined by the valency and frequency of the elements in I other than oxygen.

10. A process as claimed in claim 1, which is carried out in a tube bundle reactor.

11. A process as claimed in claim 1, wherein the increase in the temperature of the fixed catalyst bed over time is carried out in such a way that the acrolein content in the product gas mixture does not exceed 1500 ppm by weight.

12. A process as claimed in claim 1, wherein the acrolein hourly space velocity on the fixed catalyst bed is $\geq$90 l (STP)/l·h.

13. A process as claimed in claim 1, wherein the acrolein hourly space velocity on the fixed catalyst bed is $\geq$130 l (STP)/l·h.

14. A process as claimed in claim 1, wherein the CO content of the gas mixture G falls from a nonzero starting value within the period $t_G$ over which the gas mixture G is conducted through the fixed catalyst bed.

15. A process as claimed in claim 1, wherein the gas mixture G has from >0 to $\leq$20 ppm by weight of a gaseous Mo-containing compound.

16. A process as claimed in claim 1, wherein the oxygen content of the gas mixture G is increased from a lower starting value to a higher end value within the period $t_G$ over which the gas mixture G is conducted through the fixed catalyst bed.

17. A process as claimed in claim 1, wherein the increase in the temperature of the fixed catalyst bed over time is carried out in such a way that the conversion of the acrolein on single pass of the reaction gas mixture through the fixed catalyst bed does not go below 94 mol %.

18. A process as claimed in claim 1, wherein the starting reaction gas mixture contains from 6 to 15% by volume of acrolein.

* * * * *